US009907827B2

(12) United States Patent
Mercati et al.

(10) Patent No.: US 9,907,827 B2
(45) Date of Patent: Mar. 6, 2018

(54) PREBIOTIC MIXTURE (71) Applicant: ABOCA S.P.A SOCIETA' AGRICOLA, Sansepolcro (IT)

(72) Inventors: Valentino Mercati, Sansepolcro (IT); Valentina Mercati, Sansepolcro (IT); Andrea Lugli, Sansepolcro (IT); Anna Maidecchi, Sansepolcro (IT)

(73) Assignee: ABOCA S.P.A. SOCIETÁ AGRICOLA, Sansepolcro (IT)

( * ) Notice: Subject to any disclaimer, the term of this patent is extended or adjusted under 35 U.S.C. 154(b) by 356 days.

(21) Appl. No.: 14/382,702

(22) PCT Filed: Mar. 7, 2013

(86) PCT No.: PCT/IB2013/051805
§ 371 (c)(1),
(2) Date: Sep. 3, 2014

(87) PCT Pub. No.: WO2013/132456
PCT Pub. Date: Sep. 12, 2013

(65) Prior Publication Data
US 2015/0030690 A1 Jan. 29, 2015

(30) Foreign Application Priority Data
Mar. 7, 2012 (IT) .............................. RM2012A0084

(51) Int. Cl.
| A61K 36/185 | (2006.01) |
| A61K 36/886 | (2006.01) |
| A61K 36/64 | (2006.01) |
| A61K 36/53 | (2006.01) |
| A61K 36/73 | (2006.01) |
| A61K 36/63 | (2006.01) |
| A61K 36/906 | (2006.01) |
| A61K 35/644 | (2015.01) |
| A61K 31/733 | (2006.01) |
| A61K 36/28 | (2006.01) |
| A23L 29/244 | (2016.01) |
| A23L 33/21 | (2016.01) |

(52) U.S. Cl.
CPC .......... *A61K 36/906* (2013.01); *A23L 29/244* (2016.08); *A23L 33/21* (2016.08); *A61K 31/733* (2013.01); *A61K 35/644* (2013.01); *A61K 36/185* (2013.01); *A61K 36/28* (2013.01); *A61K 36/53* (2013.01); *A61K 36/63* (2013.01); *A61K 36/73* (2013.01); *A61K 36/886* (2013.01); *A61K 2300/00* (2013.01)

(58) Field of Classification Search
None
See application file for complete search history.

(56) References Cited

U.S. PATENT DOCUMENTS

| 6,203,797 | B1 * | 3/2001 | Perry | .................... | A23L 33/105 424/639 |
| 6,322,825 | B1 * | 11/2001 | Ninkov | .................... | A61K 36/23 424/725 |
| 7,615,240 | B2 * | 11/2009 | Mosjidis | ................ | A61K 36/48 424/725 |
| 7,919,123 | B2 * | 4/2011 | Xu | .......................... | A61K 9/08 424/400 |
| 2006/0068039 | A1 * | 3/2006 | Agger | .................. | A61K 31/195 424/738 |
| 2006/0105063 | A1 | 12/2006 | Hann et al. | | |
| 2008/0261916 | A1 | 10/2008 | Jaszberenyi et al. | | |
| 2008/0299258 | A1 | 12/2008 | Roman et al. | | |
| 2009/0252792 | A1 * | 10/2009 | Verbruggen | ......... | A61K 9/0065 424/474 |
| 2009/0304831 | A1 * | 12/2009 | Clement | ................ | A61K 36/28 424/757 |
| 2011/0318432 | A1 * | 12/2011 | Munafo | ................. | A61K 36/60 424/690 |
| 2012/0058095 | A1 | 3/2012 | Strozzi et al. | | |
| 2012/0121621 | A1 | 5/2012 | Jaszberenyi et al. | | |
| 2012/0269865 | A1 | 10/2012 | Roughead et al. | | |

FOREIGN PATENT DOCUMENTS

| CN | 101112439 A * | 1/2008 |
| JP | 4113242 B1 * | 7/2008 |
| WO | 2006/096161 | 9/2006 |
| WO | 2006/134409 | 12/2006 |
| WO | WO2007030902 A2 * | 3/2007 |
| WO | 2010/103374 | 9/2010 |
| WO | 2010/123351 | 10/2010 |
| WO | 2011/060123 | 5/2011 |

OTHER PUBLICATIONS

Int'l Search Report and Written Opinion for PCT/IB2013/51808, dated Jul. 9, 2013.
Anonymous "Aboca Sollievo Bio" Parafarmacia Drugstore San Domenico website, two pages of product description (Apr. 2009).
Anonymous "Agrimony" Herbal Extracts Plus electronic database, two pages (Mar. 2007).
Anonymous "Fisiodepur Concentrato Fluido—Flaconcini" Aboca L'evoluzione della Fitoterapia website, two pages of product description, (Jan. 2004).
Anonymous "Fisiodepur Opercoli" Aboca L'evoluzione della Fitoterapia website, two pages of product description (Sep. 2004).
Anonymous "Griposan balsam" Silvanols website, one page (Oct. 2011).
Anonymous "Thyme" Herbal Extracts Plus electronic database, two pages (Aug. 2006).
Ghosh & Playford "Bioactive natural compounds for the treatment of gastrointestinal disorders" *Clinical Science*, vol. 104, No. 6, pp. 547-556 (Jun. 2003).
Marzorati et al. "In vitro modulation of the human gastrointestinal microbial community by plant-derived polysaccharide-rich dietary supplements" *Int'l J. Food Microbiology*, vol. 139, No. 3, pp. 168-176 (May 2010).

* cited by examiner

*Primary Examiner* — Chris R Tate
*Assistant Examiner* — Randall Winston
(74) *Attorney, Agent, or Firm* — Nixon & Vanderhye PC (57) ABSTRACT

The present invention refers to a prebiotic mixture comprising at least one plant polysaccharide fiber and at least one of Propolis and/or *Olea europaea* and/or *Aloe vera* extracts, optionally comprising also *Thymus vulgaris* and/or *Agrimonia eupatoria* extracts. Moreover, the present invention also relates to said mixture for use in the preservation and/or in the restoration of the intestinal microbiota balance.

16 Claims, 3 Drawing Sheets

PREBIOTIC MIXTURE

This application is the U.S. national phase of International Application No. PCT/IB2013/051805, filed 7 Mar. 2013, which designated the U.S. and claims priority to IT Application No. RM2012A000084, filed 7 Mar. 2012; the entire contents of each of which are hereby incorporated by reference.

The present invention refers to a prebiotic mixture comprising at least one plant polysaccharide fibre and at least one of Propolis and/or *Olea europaea* and/or *Aloe vera* extracts, optionally comprising also a *Thymus vulgaris* and/or *Agrimonia eupatoria* extract. Moreover, the present invention also relates to said mixture for use in the preservation and/or restoration of the intestinal microbiota balance.

STATE OF THE PRIOR ART

In the literature, a large number of studies demonstrate how intestinal bacterial flora plays a relevant role on the health conditions of a subject, basically a human being (Hawrelak, J. A., & Myers, S. P. (2004). The causes of intestinal dysbiosis: a review. *Altern Med Rev,* 9(2), 180-197.). Accordingly, several research groups turned their attention to understanding the relations existing among intestinal microbiota balance and predisposition, onset and/or treatment of some pathological conditions, both intestinal and extra-intestinal ones. Commonly, intestinal (or gut) flora (microbiota) signifies the set of microorganisms resident in the alimentary tube, and that, in an adult man, consists of about $10^{14}$ bacteria and comprises from about 5000 to 10000 species of different bacteria.

Positive modulation of the intestinal flora, i.e. the preservation and/or the restoration of its balance, is currently attained by use of probiotics and prebiotics. Probiotics are defined as non-pathogenic and non-toxic living organisms that, administered in an adequate amount, give a health benefit on the host (OMS definition). Lactic bacteria (LAB, Lactic Acid Bacteria), for the most part represented by lactobacilli, and bifidobacteria are the commonest typologies of probiotic microorganisms. Instead, with "prebiotic" it is defined a substance that, when ingested, is not absorbed by the organism, but is capable of stimulating the growth and/or the activity of bacteria of the intestinal flora, conferring benefits on health (Gibson G R, Roberfroid M B. Dietary modulation of the human colonic microbiota: introducing the concept of prebiotics. J Nutr. 1995 June; 125(6): 1401-12. PMID). Prebiotics are molecules, usually oligosaccharides or polysaccharides of plant origin, such as fructo-oligosaccharides (FOS) and inulin, capable of increasing the number and/or activity of lactic bacteria (lactobacilli) and/or of bifidobacteria (Kolida et al., 2002; Kolida et al., 2007; Roberfroid et al., 2007; Roberfroid et al., 2010).

Recent studies highlighted also the existence of non-polysaccharide molecules capable of modulating the microbiota by selectively intervening on the metabolism of bacteria of different species (Lee et al. 2006). Such molecules are referred to by the term "metabolic probiotics" and among them are several classes of natural compounds, such as phenolic compounds (Selma M V et al. 2009), saponins (Patara et. al. 2009).

Various data present in the scientific literature demonstrate how the intake of polysaccharide fibres-based prebiotic compositions is scarcely tolerated by subjects intaking them, owing to the significant production of gas during the intestinal fermentation thereof. In particular, excessive $CO_2$ production in the intestine entails side effects such as intestinal swelling, also referred to as abdominal swelling, abdominal tension and pain, which cause states of general indisposition with a consequent low compliance by the subject.

In fact, it has been demonstrated that non-tolerability partly depends on fibre structure; e.g., short fibres and/or fibres with bonds that can be easily attacked are fermented more quickly, leading to a sudden production of gas with the entailed relative discomfort.

PCT Patent Application No. WO2011/060123 relates to nutritional compositions comprising fibres, such as FOS and inulin, and a long-chain polysaccharide (like acacia gum) and their use for the restoration of intestinal microflora. In particular, such composition is indicated to be better tolerated by the subject ingesting it, with respect to compositions containing only FOS and inulin, since the polysaccharide modifies the intestinal fermentation from a boost fermentation in the proximal colon into a gradual fermentation in the complete colon ([00242] and [00262]). According to the above-cited PCT Patent Application, to increase tolerance to fibre-comprising compositions a long-chain polysaccharide should be added.

Therefore, from the known state of the art it emerges that the assessment of total production of gas in the intestine is an important aspect to consider in estimating the side effect-benefit ratio of a nutrient composition comprising natural polysaccharide fibres.

The present invention aims at singling out a novel and original solution to the problems present in the known state of the art and linked to polysaccharide fibre intake.

SUMMARY OF THE INVENTION

The present invention relates to a prebiotic mixture comprising at least one plant polysaccharide fibre and at least one of *Olea europaea* and/or Propolis and/or *Aloe vera* extracts, a *Thymus vulgaris* extract and a *Agrimonia eupatoria* extract; compositions comprising it and their use as prebiotics for the treatment of gastrointestinal pathologies wherein an alteration of intestinal bacterial flora is present.

In fact, the Inventors have surprisingly discovered that the mixture described herein, besides enhancing the prebiotic effect of the fibre, does not entail the side effects normally found in the use of plant fibres as prebiotics. In fact, studies conducted by the Inventors demonstrated that the presence of the above-cited extracts in association with one or more plant polysaccharide fibres, delays fibre fermentation kinetics, avoiding to the patient the abdominal pains associated with a sudden gas generation normally developed from polysaccharide fibres.

The Inventors also demonstrated that the mixture of the invention is capable of enhancing the prebiotic effect of the fibres and has a high prebiotic effect with a clear bifidogenic activity, and that the combination of the selected extracts delays also the kinetics of gases developed in the intestine.

It was found that the association between at least one of such extracts and a plant polysaccharide fibre determines a significant increase of the bifidogenic effect observed, and at times even a synergistic bifidogenic effect between extract and fibre on the intestinal bacterial flora. In particular, said synergistic effect is observed in connection with the growth of bifidobacteria that are described in the literature as bacteria having beneficial properties. The mixture described herein, therefore, comprises a selection of ingredients that, besides improving the prebiotic effect of fibres contained therein, is capable of improving the subject's tolerability thereto thanks to the delaying of the fermentation kinetics exerted by the fibre-associated extracts.

Moreover, the *Olea europaea*, Propolis, *Aloe vera*, *Thymus vulgaris* and/or *Agrimonia* (or *Agrimonia eupatoria*) extracts in association with the fibres, by boosting the prebiotic activity of the same, enable first of all to limit fibre intake (i.e., prebiotic effect being equal, for instance in bifidobacteria increase, the association of fibres+extracts according to the description, by increasing the prebiotic effect of the fibres themselves, enables to reduce the amount of fibres intaken) thereby decreasing the undesired side effects, and, moreover, further decrease the side effects by delaying the gas development kinetics caused by the presence of fibres, thereby decreasing intestinal pains.

Therefore, object of the present description is a prebiotic mixture comprising at least one plant polysaccharide fibre and at least one of *Olea europaea*, and/or Propolis and/or *Aloe vera* extracts and a *Thymus vulgaris* and/or *Agrimonia eupatoria* extract, compositions comprising said mixture and use thereof (of the mixture or the composition) in the prevention and/or the treatment of gastrointestinal pathologies exhibiting an alteration of the intestinal flora balance, concomitantly delaying and/or inhibiting the formation of gas in the intestine related to the presence in the composition of fibres having a prebiotic effect.

In such pathologies, the capability of the mixture and of the composition of delay or inhibiting the formation of intestinal gases is particularly useful, as those lack painful side effects due to a sudden development of gas in the intestine caused by a component having a strong prebiotic activity (i.e., the fibres).

DESCRIPTION OF THE FIGURES

Inulin HP: inulin with a high degree of polymerization; Inulin GR: inulin from chicory; CN: negative control; Propolis+inulin GR: mixture of Propolis extract (0.1%) and inulin GR (1%); *Aloe*+inulin GR: mixture of lyophilized *Aloe* gel (0.1%)+inulin GR (1%); Olive+inulin GR: mixture of Olive extract (0.1%)+inulin Gr (1%); Mix+inulin GR: 0.1% of mixture of Olive, Propolis, and thyme extracts, in equal proportions+inulin GR (1%).

The graph compares the bifidogenic effect of various mixtures followed for 24 hours, sampling for measuring the number of bifidobacteria at time 0, at 4 hours, 8 hours, and 24 hours. The figure shows the synergistic bifidogenic effect of the association of Propolis, thyme, olive or aloe extracts with inulin GR. Positive control is represented by inulin extracted from chicory (GR), over 24 hours, starting from introduction of the mixtures to be tested in the "Batch culture" experimental model.

All mixtures contain Inulin GR or HP as indicated (1%), plus optionally a (0.1%) extract of Propolis (prop), thyme, olive, aloe, or a mixture of extracts (always a 0.1% mix.) comprised, in equal parts, of thyme, Propolis, olive extracts. A statistically significant difference is highlighted with  or * ( $p<0.01$; * $p<0.001$) between the number of bifidobacteria at 24 hours and time 0.

All mixtures contain (1%) Inulin GR (apart from the negative control which has only faeces) plus optionally an extract of (0.1%) agrimonia (Agrim), Propolis (Prop), Olive, or mixtures (always 0.1%) of the same extracts present in equal parts.

With * it is highlighted a statistically significant difference ($p<0.05$) between the number of bifidobacteria at 24 hours and at time 0.

FIG. 5:

"Gut Model", assessment of the bifidogenic effect of an extract rich in mucilages from *Althaea*.

In the abscissae, reactors 1, 2, 3 simulate in the model the ascending, transverse and descending colon. In the ordinates, the number of bifidobacteria, expressed as logarithm, at the reaching of the initial stationary state, and after introduction of the *Althaea* extract and upon reaching the final stationary state.

The *Althaea* extract is bifidogenic in all three reactors, inducing a statistically significant increase of bifidobacteria (* $p<0.05$; ** $p<0.01$)

DETAILED DESCRIPTION OF THE INVENTION

The present invention relates to the association of fibres of polysaccharide nature, having prebiotic activity, and plant extracts which increase the prebiotic activity of said fibres and inhibit or delay the formation of intestinal gases caused by said fibres.

In particular, herein it is described a prebiotic mixture comprising at least one plant polysaccharide fibre and at least one of *Olea europaea* and/or Propolis and/or *Aloe vera* extracts and a *Thymus vulgaris* and/or *Agrimonia eupatoria* extract.

It is to be understood, within the scope of the present description, that in connection with the embodiments in which the components of the composition are indicated, as to the active principles selected the term "comprises/comprising" could also be replaced by the term "consists/consisting in". Therefore, the term comprises/comprising in connection with a selection of active principles as indicated herein could be understood as consisting in said active principles and optionally comprising excipients suitable for the desired formulation.

"Prebiotics" in the present description signifies non-digestible organic substances or mixtures comprising such substances, capable of selectively stimulating the growth and/or the activity of one or of a limited number of beneficial bacteria present in the colon.

The prebiotic effect of the mixture described herein is concretized in the non-absorption in the intestine of one or more components of the mixture and in the stimulation of the growth and/or the activity of intestinal flora bacteria described as beneficial on health. Specifically, among "beneficial" bacteria present in the intestine, the mixture according to the invention stimulates bifidobacteria and/or lactobacilli deemed in the literature as pre-eminently "probiotic" bacteria.

The use of a mixture or a prebiotic composition also has a recognized medical effect, due to the fact that the prebiotic stimulates intestinal flora growth and/or activity, compromised in several gastrointestinal pathologies, essential to a subject's well-being.

The term "mixture" in the present description signifies a set of various components; these could be in any suitable state, like e.g. in a solid, semi-solid, powder, semi-liquid, liquid state, in an emulsion, etc. Therefore, for instance, the prebiotic mixture in its most general embodiment could comprise polysaccharide fibres in their solid, semi-solid and/or liquid form, together with the extracts indicated herein, them also in solid, semi-solid and/or liquid form.

The term "plant polysaccharide fibre" indicates a complex mixture of various polymers, branched and unbranched, made up by the union of a series of monosaccharides. A non-limiting example of such a fibre is inulin, comprised of fructose monomers and present in *Cichorium* spp. plants, like e.g. *Cichorium intybus* L. (Common chicory) or *Helianthus tuberosus*. In the present description the general terms "fibre" or "plant fibre", when utilized, always refer to a "plant polysaccharide fibre", unless otherwise indicated.

In the mixture of the present description any plant polysaccharide fibre falling within the above definition could be utilized, like e.g. plant fibres selected in the group comprising inulin, mucilages of Malvaceaes, flea-worth fibres, mucilages from *Linum usitatissimum*, glucomannan fibres, spear grass fibres and gum arabic. Such fibres will be described in more detail below.

The term "extract" in this description refers to a set of substances of plant/natural origin obtained by extraction processes from entire plants or parts thereof. Such methods are conventional and well-known to the average technician in the art; therefore, neither an in-depth analysis, nor a detailed description of known technologies are necessary to realize the invention described herein.

Studies conducted by the Inventors of the present invention highlighted that the association of at least one polysaccharide fibre and one or more plant extracts selected among those described herein enables to realize an effective instrument for intestinal microbiota modulation in a broader manner (with respect to the use of the sole fibres).

Moreover, it was discovered that specific extracts, in association with polysaccharide fibres, induce a delay in the formation of intestinal gases caused by fibre presence, thereby reducing, when introduced in a mixture having prebiotic activity, a known and painful side effect associated with the ingestion of plant polysaccharide fibres.

As reported above, a problem associated with the use of polysaccharide fibres as prebiotics, reducing their tolerability by subjects intaking them, is caused by a fermentation thereof in the intestine, entailing a rapid formation of gas with consequent intestinal swelling and abdominal pain. The Inventors of the present invention demonstrated, as is evident from the examples below, that when at least one of *Olea europaea* and/or Propolis and/or *Aloe vera* extracts and a *Thymus vulgaris* and/or *Agrimonia eupatoria* extract are associated with a fibre as described herein, the fibre fermentation kinetics is delayed. In other terms, a decrease in the production of gas in the intestine in the first hours post-ingestion was demonstrated, entailing, therefore, a greater tolerability of the fibre contained in prebiotic mixtures.

Figure 1:
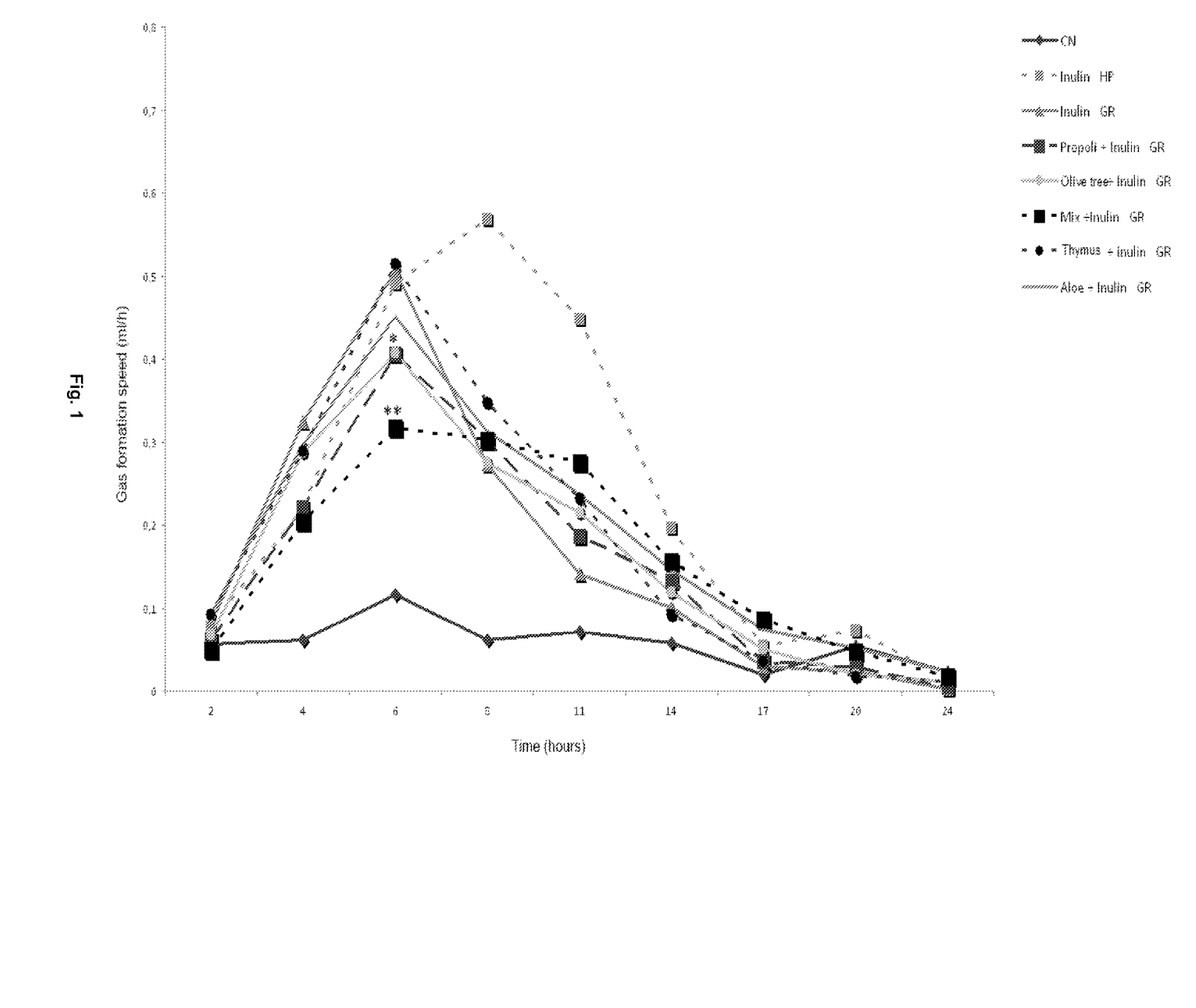
FIG. 1: gas formation kinetics over time in the intestine, following intake of polysaccharide fibres or of embodiments of the prebiotic mixtures according to the present invention. CN=negative control; GR=inulin from chicory; HP=long-chain inulin from chicory; Mix=mixture of Propolis, thyme and olive extracts.
Figure 2:
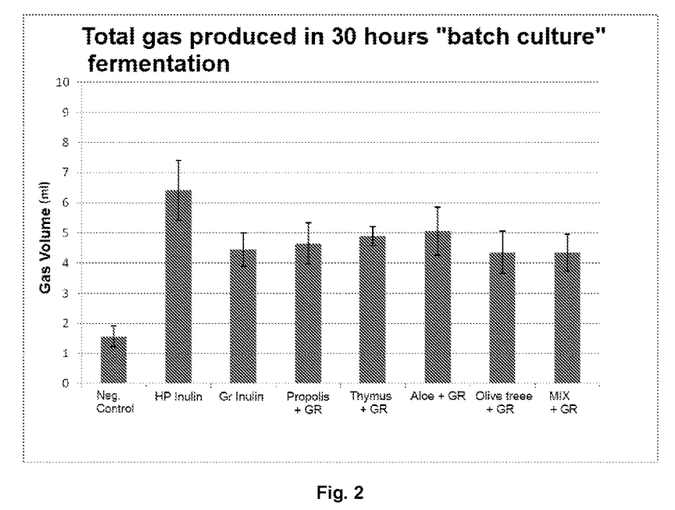
FIG. 2: Amount of gas formed in 30 hours of fermentation following simulation of intake of inulin and at least one of *Olea europaea*, Propolis, *Thymus vulgaris* and *Aloe* extracts.

As is evident from FIG. 1 and FIG. 2, the amount of gas developed overall does not seem to vary in a specific manner, whereas the time needed to the development of such gases, development which is sensibly delayed by the components of the mixture described herein, varies substantially. Such a delay over time prevents a sudden intestinal swelling, with the well-known pains associated to the latter. A delay over time in the formation of gas enables an improved tolerability in plant fibres intake to the treated subject.

The delay of the gas formation kinetics described herein and shown in FIG. 1 was totally unforeseeable on the basis of the known art.

Figure 3:
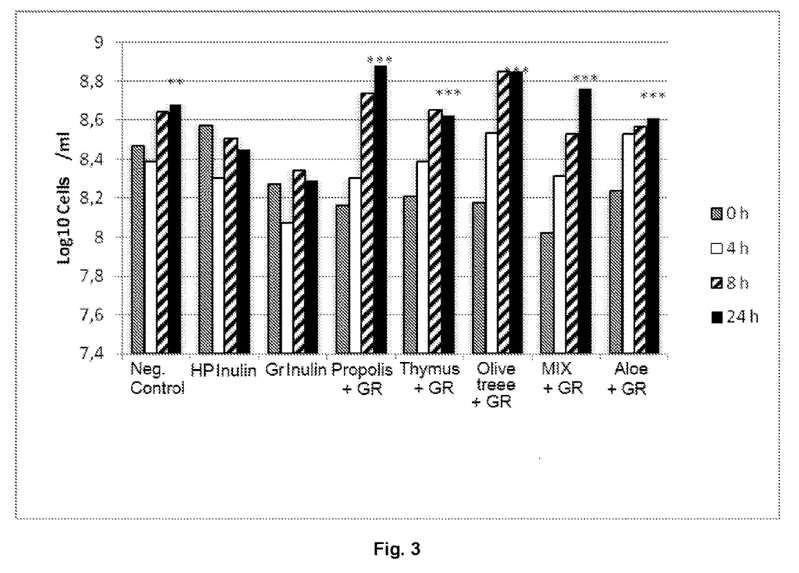
FIG. 3: Batch Culture Model, assessment of the bifidogenic effect of various mixtures.
Figure 4:
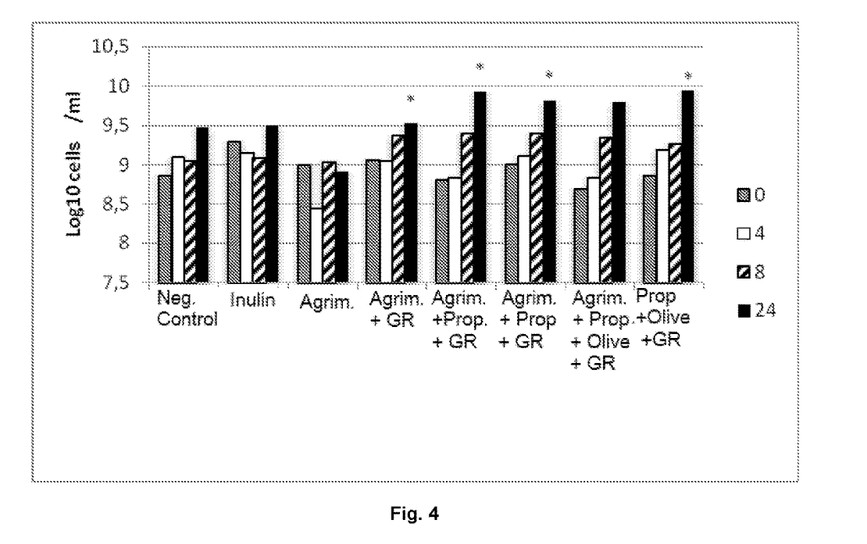
FIG. 4: Batch Culture Model, assessment of the bifidogenic effect of various mixtures. The graph compares the bifidogenic effect of various mixtures followed for 24 hours, sampling for measuring the number of bifidobacteria at time 0, at 4 hours, 8 hours, and 24 hours.
Figure 5:
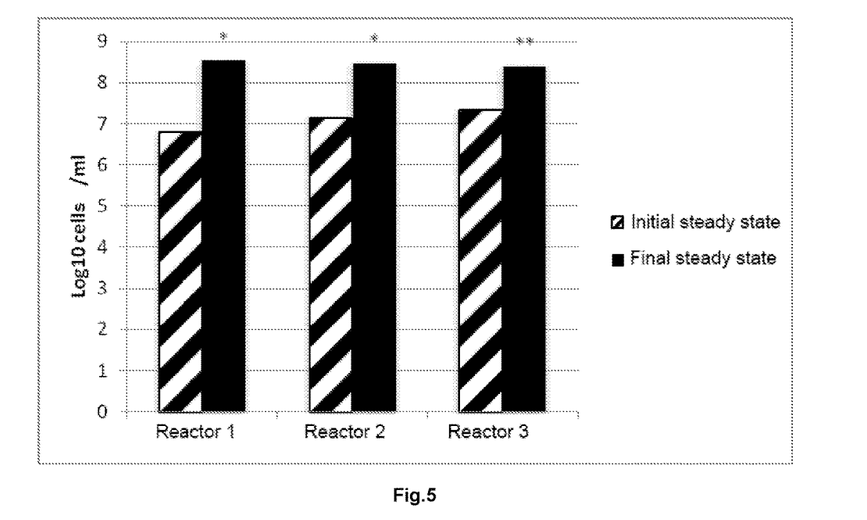

Moreover, it was also found, as is evident from FIGS. 3-5, that the prebiotic effect of the polysaccharide fibre/s is increased when it/they is/are associated to at least one of the extracts indicated in the present description, showing a synergy between the prebiotic effect of the plant fibre and that of the extract.

This synergy indirectly has positive repercussions also on the issue of tolerability associated to ingestion of the sole fibres, since it is possible to increase the prebiotic activity of the mixtures described herein without increasing fibre intake. I.e., prebiotic effect being equal (e.g. in the increase of bifidobacteria or of their activity), the association of fibre/s+extract/s according to the present description enables to reduce the amount of fibre/s intaken.

According to an embodiment of the invention, the extracts to be utilized in association with at least one fibre are *Olea europaea*, and/or Propolis and/or *Aloe vera* extracts and a *Thymus vulgaris* and/or *Agrimonia eupatoria* extract.

*Olea europaea* is the common olive tree (in this disclosure also referred to simply as "olive" or "olive tree") whose extracts are commonly used in the cardiovascular field, e.g., in the controlling of arterial pressure. Moreover, various data in the literature also demonstrate antimicrobial properties on various bacteria and fungi, antioxidant activities, and astringent properties.

Propolis is a resinous substance that bees collect from various plant sources, consisting of the mixture of more than 300 different constituents. In the literature it is described that Propolis comprises biologically active constituents implied in a wide range of pharmacological properties, in particular antimicrobial, antiinflammatory, antifungal, antiviral, hepatoprotective, antioxidant, antitumor activities.

*Aloe vera* is a plant of Aloeaceae family, described above all for topical use, to bring relief in case of burning sensation from burns. Moreover, some studies demonstrate its activity as fungicide, antipyretic and anti-inflammatory. To the ends of the present invention, extract of foliar gel (even dehydrated) could be utilized as extract for the aloe.

Curiously, despite the antimicrobial properties reported for the above-described substances, a prebiotic effect of the same was observed in association with the fibres, i.e. an effect assisting in the intestinal survival of beneficial bacteria.

According to the present invention, Propolis will be associated to the fibre preferably in the form of a hydroalcoholic extract, whereas for the olive (tree) an extract obtained from its leaves will preferably be utilized. Besides the association between fibre and/or Propolis and/or olive extracts, in an embodiment of the invention the mixture comprises *Thymus vulgaris* and/or *Agrimonia eupatoria*, them also capable of assisting and increasing the prebiotic activity of fibres as described herein.

*Heliantus tuberosus* (in this description also referred to simply as "Jerusalem artichoke"), is an annual herbaceous plant of the Esteraceae family known for the high content of fructans, in particular of inulin. To the ends of the present invention, the extract obtained from the tuber and/or from the top could be utilized as a source of fibres.

*Thymus vulgaris* (in this description also referred to simply as "thyme") is an aromatic herbaceous plant of the Lamiaceae family, known essentially for its antioxidant, antiseptic, carminative, expectorant properties. To the ends of the present invention, a leaf extract could be utilized.

*Agrimonia eupatoria* is a perennial herbaceous plant, known in particular, for external use, against conjunctivitis, oral and nasal cavity inflammations, and in general against a vast number of skin diseases, thanks to the presence in its extract of an acid (ursolic acid), with an activity comparable to cortisone. Internally, it is traditionally utilized as an astringent. To the ends of the present invention, the *Agrimonia* extract preferably could be extracted/obtained from the top of the plant.

Evidently, the extracts from the various plants indicated in the present description can be obtained by any one extraction process known to a technician in the field and described in laboratory manuals, like e.g. (without limitation) conventional methods suitable for obtaining hydroalcoholic extracts from plant material. Merely by way of illustration and without limitative purposes, the extraction could be conducted by treating resin or plant parts with 20%, or 30%, or 40%, or 50%, or 60%, or 70%, or 80% hydroalcoholic solutions; wherein the alcohols may be, e.g., methanol, ethanol, isopropanol or other alcohols commonly utilized in these protocols. In a specific embodiment, ethanol will be used. Normally, the alcoholic extract obtained is subsequently subjected to filtration, concentration, and optional drying to provide the corresponding dry extract.

The properties known in the literature for the extracts from the plants described herein add to the prebiotic effect described herein also properties such as anti-inflammatory, antipyretic, antioxidant ones, etc., according to which further extract/s is/are present in the mixture described herein. Therefore, besides the effect not known, and described for the first time herein, related to the preservation and/or restoration of the intestinal bacterial flora connected with the reduction in the formation of intestinal gas, the embodiments of the mixture in accordance with the present invention can also have further desirable effects depending on the specific component present therein.

As indicated above, the mixture comprises as main ingredient at least one plant polysaccharide fibre which may be selected in the group comprising inulin, mucilages of Malvaceaes, like e.g. from *Malva* spp. or from *Althaea* spp., flea-worth fibres, mucilages from flax, glucomannan fibres, scutch grass (*Cynodon Dactylon*) and/or gum arabic.

Inulin is a known oligosaccharide formed by β-D fructose monomers, obtained or obtainable, e.g., from epigeal and hypogeous parts of different plants such as *Cichorium intybus* and/or *Helianthus tuberosus* and/or *Cynara scolymus* and/or *Taraxacum officinalis* and/or *Arctium lappa*. Besides those listed above by way of illustration, any known inulin is suitable for realizing the present invention.

To the ends of the present invention, suitable fibres could be represented also by fibres present in the mucilages of plants belonging to the Malvaceaes family, plants that, as is well-known, contain mucilages in different parts such as leaves, flowers and roots. Specific examples of such mucilages are, e.g., mucilages from *Malva silvestris, Althaea officinalis, Hibiscus* spp.

Therefore, in an embodiment of the invention, fibres present in the mucilages from *Althaea officinalis*, which is a plant traditionally used as lenitive of mucosae, both of the digestive tract and of the pharynx, could be utilized. Its phytocomplex, extracted from root and/or leaves, contains abundant mucilaginous fibres whose composition is partly known. About the 80% of the fibres is comprised of acid or very acid mucilages, due to the presence of galacturonic and glucuronic acid. Also a soluble arabinan, having a highly branched structure, and 3 glucans were isolated. In particular, *Althaea* root, as is known, provides aqueous extracts rich in mucilaginous components. To the ends of the present invention, the mucilages utilized in the mixture described herein can therefore be obtained from *Althaea* root and/or leaves. The Inventors of the present invention also demonstrated that such fibres, and in general the fibres described herein, have prebiotic activity. For instance, the fibres present in mucilages from *Althaea* (e.g., root) have a prebiotic activity preferentially towards bifidobacteria.

Then, the extracts (mucilages) from *Althaea* already as such show the ability to stimulate bifidobacteria growth, enabling to modulate the balance of intestinal bacterial flora, as it also results from an in vitro model referred to as "gut model", illustrated in example 2 reported below.

Likewise, also fibres from leaves of *Malva officinalis, Hibiscus* spp. and other Malvaceaes commonly used in the herbal field are suitable.

The fibres indicated in the present description share the fact of showing an increase of prebiotic effect in association with the above-described extracts.

Among the other fibres suitable for making the mixture of the invention there are also gum arabic, which is a complex mixture of polysaccharides (M.W.: 250,000-300,000) and glycoproteins, also known as acacia gum, as extracted from two sub-*Saharan acacia* species: *Acacia senegal* and *Acacia seyal*; flea-worth fibres, obtainable from seeds or cuticles of *Plantago psylium* and/or *Plantago indica* and/or *Plantago ovata*; fibres present in mucilages from *Linum usitatissimum*; glucomannan fibres (fibres from the *Amorphophallus konjac* tuber); and spear grass fibres that are, e.g., obtainable from the rhizome of *Cynodon dactylon* and/or *Elymus repens*.

In the embodiments of the prebiotic mixture described according to the invention, the above-described polysaccharide fibres may be present individually or in a combination of two or more fibres. For instance, in the prebiotic mixture only inulin or mucilages of Malvaceaes (e.g. *Althaea*, mallow) or mucilages from *Linum* or flea-worth fibres or glucomannan fibres or gum arabic or scutch grass (*Cynodon dactylon*) could be present, or, alternatively, combinations thereof like, e.g., inulin and mucilages; or again inulin, gum arabic and mucilages; inulin, glucomannan fibres, etc., could be present. The term "inulin or fructooligosaccharides from different origin" in the present description signifies a mixture of inulin molecules or a mixture of fructooligosaccharides derived from fructans contained in various plants, such as e.g. Jerusalem artichoke, chicory, burdock, dandelion, artichoke. The mixture could comprise any association between one or more polysaccharide fibres and at least one extract selected from olive extract and/or Propolis extract and a *Thymus vulgaris* and/or *Agrimonia eupatoria* extract.

In a particularly interesting embodiment, the mixture will comprise olive extract and/or Propolis extract, inulin, mucilages from *Althaea* and gum arabic, a *Thymus vulgaris* extract and an *Agrimonia eupatoria* extract.

The above-described mixture could further comprise extracts from plants having a prokinetic effect, accelerating the transit of the mixture itself in the intestinal tract, like e.g. ginger.

In an embodiment of the invention, the fibres will be from about 50% to about 90% by weight of the mixture, like e.g. at least the 50, 60, 65, 70, 75, 80, 81, 82, 83, 84, 85, 86, 87, 88, 89, 90% by weight of the mixture and the extracts will be between 5 and 25% by weight of the mixture, like e.g. at least the 5, 10, 12, 14, 16, 18, 20, 22, 24, 26, 28, 30, 35, 40, 45, 50% by weight of the mixture.

It is specified here that every time the present description provides a numerical range expressed in percent, all integers and all decimal numbers up to two digits existing within this interval, extremes included, are understood to be punctually and explicitly described. The interval is indicated as such merely in order to avoid long numerical strings that the technician in the field anyhow knows how to count in intervals as those indicated above.

In an embodiment of the present invention, the mixture (or composition comprising it) could comprise further components like, e.g., ingredients having prebiotic and/or probiotic activity, ingredients active against constipation, ingredients active against abdominal swelling, ingredients active against diarrhoea, or plants and extracts useful in various dyspeptic forms. Non-limiting examples of such further components are various typologies of dietary fibres, even non-prebiotic ones (e.g. bran, cellulose, hemicellulose, pale prickly pear fibre and the like), plants and extracts having carminative activity (e.g. fennel seeds, coriander seeds, vegetable carbon, etc.), plants and extracts rich in compounds having an antiseptic and astringent activity (e.g., plants and extracts of the Rosaceae family), stomachic and/or bitter plants (e.g., artichoke, peppermint, gentian, etc.).

It will be apparent to a technician in the field that the prebiotic mixtures described herein can comprise also further ingredients such as diluents, carriers, binders, aromatizers, sweeteners, etc., and that mixtures thus formulated fall anyhow within the scope of the present invention.

In an embodiment such further ingredients could be them also of plant origin.

The mixture of the invention could, e.g., comprise:
Inulin (from various origins): 5-90%
Gum arabic: 5-30%
Thyme leaf extract: 1-7%
Propolis extract: 1-7%
Olive leaf extract: 1-9%
*Althaea* extract: 2-20%
Or
Gum arabic: 5-90%
Glucomannan: 5-30%
Lime tree mucilaginous extract: 2-20%
Olive leaf extract: 1-20%
*Agrimonia* top extract 1-9%
Or
Fructooligosaccharides (from different origins): 5-90%
*Agrimonia* extract: 1-9%
Propolis extract: 1-9%
Or
Inulin from different origins: 5-90%
Olive extract: 1-9%
Propolis extract: 1-9%
Fennel fruits: 1-10%
*Rosa* spp. Flowers: 2-20%
Or
Inulin or FOS from different origins: 5-90%
Thyme leaf extract: 1-9%
Olive leaf extract: 1-9%
*Malva* leaf extract: 3-20%
Or
Flea-worth seeds or cuticle: 5-90%
Propolis extract: 1-9%
*Agrimonia* extract: 1-9%
Coriander fruit extract: 1-10%

The prebiotic mixture could be formulated in any way deemed suitable by the technician in the field for the objects illustrated herein. In particular, suitable formulations for oral use could be in the form of a capsule, a tablet, a lozenge, a granulate, a powder, a syrup, an elixir, a hard gelatine, a soft gelatine, a suspension, an emulsion, a solution, etc. It is clear that any other formulation, e.g. of enteral type, even if not described, is to be construed as part of the present disclosure.

In specific embodiments, the composition or the mixture according to the invention could be made in the form of a pharmaceutical composition or of a medical device according to any one of the classes described in the Medical Devices Directive 93/42/EEC (comprising also substances and not only "devices" in the mechanical sense of the term), or in the form of a food for special medical purposes, or in any other form according to the regulatory provisions of the Country in which said composition will be produced.

The compositions could also be made in the form of dietary supplement, food for special medical purposes or nutraceutical as such, or adding one or more excipients and/or food ingredients. There are no particular limitations in the making as supplement, food, or nutraceutical, according to the present description, and all forms commonly used by the technician in the field whose preparing does not eliminate the activity of the active principles used are suitable.

As supplement, the mixture or the composition could be made in a solid, semisolid, gelatinous or liquid form, like e.g. in the form of bars, candies, jellies, beverages (suspensions or emulsions) or in the form of more complex foods, whose preparing does not deteriorate the active principles of said composition. A non-limiting example of such nutraceuticals could be represented, e.g., by liquid beverages such as shakes, juices, soft drinks, or foods such as candies, biscuits, powders, granulates, bars, etc. The composition could also be introduced at the most suitable moment of the preparing, in a liquid or dried form, in liquid or solid foods, like the technician in the field for the making of food supplements could define in a simple way and without use of inventive activity.

Object of the present invention are also foods comprising said mixture or composition in which the active principles present in the latter be not made inactive by the preparing. The dietary supplement or the food for special medical purposes could also contain ingredients, other components comprising, e.g., combinations of vitamins, mineral salts, and other substances aimed at supplementing the diet.

The various components of the mixture as heretofore-defined, i.e., at least one polysaccharide fibre and at least one of olive and/or Propolis and/or *Aloe vera* extracts, can be present in the formulation as lyophilized extracts, liquids, granulates, semisolids, gels.

For instance, the mixture could be formulated in one of the solid forms described above (tablet, pill, lozenge, capsule, etc.) wherein one or more of the individual components are present in the lyophilized state.

On the basis of the results of the above-reported experiments, the prebiotic mixture described herein is effective in the (even only partial) delaying and/or inhibiting the formation of gas in the intestine caused by fibre fermentation. In particular, when the mixture comprises an association of inulin together with Propolis, thyme and olive extracts, gas production due to inulin fermentation in the intestine is drastically decreased as indicated in FIG. 1.

The mixture described herein can be advantageously utilized for the preservation and/or restoration of the intestinal bacterial flora. Taking into account the ability of the extracts, both alone and in association with at least one fibre, to induce stimulation of bacteria of the microbiota, the mixture could be particularly effective and its prebiotic activity linked to fibres could be increased by that linked to the presence of one or more among the extracts described herein. In particular, in one embodiment, the use of the mixture or of the composition could be addressed to the growth of bacteria such as Bifidobacteria.

In the last years, an alteration of the balance of the intestinal bacterial flora has been associated to the onset, or also to the presence of various intestinal and extra-intestinal pathologies. Therefore, the prebiotic mixture described herein can be validly employed for the prevention and/or the treatment of gastrointestinal pathologies showing an alteration of the intestinal flora balance or of gastrointestinal pathologies having, among their most evident symptoms, such an alteration. By way of example and not for limitative purposes, such pathologies can be selected in the group comprising: diverticulosis, SIBO (small intestine bacterial overgrowth), IBD (inflammatory bowel disease), IBS (irritable bowel syndrome), diarrhoea (e.g., traveller's diarrhoea), various dyspeptic forms, intestinal swelling, meteorism, prevention of diarrhoea caused by antibiotic intake, food allergies, alteration of immune system defences.

The mixture could also be utilized for the delay and/or the inhibition of the formation of gas in the intestine, comprising a step of administering the prebiotic mixture described herein.

In a further aspect the invention relates to: a method for the delay and/or the inhibition of the formation of gas in the intestine due to prebiotic fibre intake, comprising one or more steps of administering the mixture or the composition described herein; a method of treatment aimed to the preservation and/or restoration of the intestinal bacterial flora, comprising one or more steps of administering the prebiotic mixture or the composition described herein, and also a method for the prevention and/or the treatment of gastrointestinal pathologies characterized by alteration of the intestinal flora balance, comprising one or more steps of administering the mixture or the composition of the invention.

In an embodiment, the method is for the prevention and/or the treatment of ISB (irritable bowel syndrome) and comprises the administration of the composition described herein to an individual in need thereof.

Gastrointestinal pathologies in which an alteration of microbiota balance is observed, which may be prevented and/or treated with the mixture or with the composition described herein, may be selected in the group comprising diverticulosis, SIBO (small intestine bacterial overgrowth), IBD (inflammatory bowel disease), IBS and traveller's diarrhoea, various dyspeptic forms, intestinal swelling, meteorism, diarrhoea caused by antibiotics, food allergies, alteration of immune system defences.

A non-limiting example of the method of treatment and/or prevention of the pathologies reported above, could comprise the administration of a daily dosage, subdivided into a single dose or in plural doses, of the mixture or of the composition according to the present description, for a time period comprised between one and six weeks, e.g. comprised between three and six weeks or even for a time period longer than six weeks, depending on the judgment of the doctor in charge.

The doctor in charge will be able to define both the most suitable dosage and the administration times, also based on the patient's state of health, weight, gender and age.

An exemplary form of treatment envisages the administration of the above-described compositions one or more times per day, e.g. from one hour before meals or even during meals.

A non-limiting example of daily dosage suitable for the above-indicated treatments is
fibres, about 1000-2000 g/die
Propolis, lyophilized extract (EL), abt. 30-80 mg/day
olive, lyophilized extract (EL), abt. 100-200 mg/day
thyme lyophilized extract (EL), abt. 100-200 mg/day
Total of lyophilized extracts (thyme+olive+Propolis) per tablet: abt. 230-480 mg/day.

Moreover, the invention relates to a method for the preparation of a mixture as described herein, wherein said at least one plant polysaccharide fibre and at least one of *Olea europaea* and/or Propolis and/or *Aloe vera* extracts are mixed together with a *Thymus vulgaris* and/or *Agrimonia eupatoria* extract and optionally with one or more of the above-described additional components and/or with one or more excipients and/or with one or more aromatizers in a single step or in successive steps.

The mixing techniques selected will be functional to the form in which the composition is to be made; in case tablets or lozenges are to be made, also at least one step of pressing, etc.

For instance, the extracts as described above could be mixed together with a mixer commonly employed in pharmaceutical practice, such as a cone, a double-cone, a four-way one, allowing homogeneous mixing of the components. Then, it is carried out a granulation, which may be performed with a technique described in patent EP1584240A1, or by employing conventional high-speed, fluid-bed granulators. Then, a compression is carried out according to techniques known to a person of average skill in the art.

EXAMPLES

1. Prebiotic Activity Demonstration

The in vitro model utilized to study the prebiotic activity of embodiments of the prebiotic mixtures according to the present invention is the "Batch Culture" model: In particular, it is a reactor simulating the physiological conditions present in the colon. In the model inoculated with the mixtures to be tested, a positive control and a negative control according to the scheme reported below, microbiota evolution over 24 hours subsequent to inoculation is observed. In particular, through FISH technique it is possible to single out the quantitative evolution of given bacterial strains or classes over 24 hours.
Negative control: faeces only
Positive control: chicory inulin (HP, high degree of polymerization), average DP (polymerization degree): ≥10 (1%)
Positive control: chicory inulin GR, average DP: >23 (1%)
Tests: 1% Inulin GR+0.1% lyophilized extract (individual extracts or in mixture).
Mixtures (#5) (for all tests, 0.1% extract+1% Inulin GR)
Propolis extract
Thyme extract
*Aloe* extract
Olive extract
Propolis+Thyme+Olive (in equal parts)
Assessment of the prebiotic/bifidogenic effect was performed by analysis of the growth of intestinal bacteria with beneficial properties, such as Lactobacilli and Bifidobacteria, by FISH technique on nucleic acids extracted from faecal samples incubated with the above-defined mixtures. Such a technique, known as "Fluorescence In-Situ Hybridization" is based on the use of molecular oligonucleotide probes, rRNA-specific for the microorganism of interest, which bind complementary segments of the gene complement and impart to the cell a fluorescence detectable by microscopy.

All tests were conducted in triplicate on three samples of faeces from three different donors.

As shown in FIG. 3, the association between the individual extracts (Propolis, thyme or olive) and inulin GR determines a statistically significant increase of bifidobacteria growth with respect to the same growth observed with the sole inulin. Moreover, also the various mixtures comprising one or more extracts and inulin GR show a positive effect on bifidobacteria growth greater than that observed with the sole inulin GR.

FIG. 4 shows the results obtained when bifidobacteria growth was assessed relative to the following samples:
1. negative control
2. 1% inulin GR
3. 0.1% lyophilized *Agrimonia*
4. 1.0% *Agrimonia*+1% inulin GR
5. 0.1% mixture (*Agrimonia*+Propolis, 1:1) and 1% inulin GR
6. 0.1% mixture (*Agrimonia*+Olive, 1:1) and 1% inulin GR
7. 0.1% mixture (*Agrimonia*+Propolis+Olive, 1:1:1) and 1% inulin GR
8. 0.1% mixture (Olive+Propolis, 1:1) and 1% inulin GR In particular, it can be seen how, from a comparison between samples 3 and 4, it is evident that the inulin+*Agrimonia* association entails an increase in the bifidogenic activity of inulin itself.

In conclusion, said data demonstrate that the association between inulin and at least one extract (thyme, olive, Propolis, *Agrimonia*) has a prebiotic effect on intestinal bacterial flora, and that said effect is a synergistic-type effect, since inulin prebiotic properties are increased in the presence of at least one extract.

2. Prebiotic Activity of *Althaea* Extract

The prebioticity study on *Althaea* was conducted by using a validated in vitro model denominated "Gut-model", an equipment consisting of three fermentation vessels in series, simulating: the first one, the ascending colon, the second one, the transverse colon, and the last one, the descending colon. The Gut model was inoculated with the flora of human subjects, concomitantly ensuring all conditions typical of the three parts of the colon: pH, nutritional elements, temperature, etc. The Gut model was then "fed" with an extract rich in *Althaea* mucilages and, upon reaching a steady state, the changes induced by the extract on the bacterial flora, production of gas and of short-chain fatty acids were observed. The main results obtained on the *Althaea* extract rich in mucilages are, as is evident from FIG. 5:
the extract has prebiotic activity, as it leads to a preferential increase of bifidobacteria.
The present study is the first in vitro test, in the "Gut model", highlighting a prebiotic activity of a mucilage-rich *Althaea* extract.

3. Demonstration of Delay of Gas Formation Kinetics

Substrate fermentation profile was assessed in test tubes for anaerobic culture, using the gas production technique described by Theodorou et al. (1994). Each test tube includes the mixture to be tested (see below for details), anaerobic pre-reduced basal medium and faeces. The test tubes were sealed and incubation was conducted at 37° C. under continuous stirring. Subsequently, test tubes internal pressure was measured by means of a manometer at different time intervals over 24 hours.

The test tubes contained one of the following samples:
CN: negative control
HP (long-chain inulin from chicory) positive control
GR (inulin from chicory) positive control
Propolis+GR
thyme+GR
aloe+GR
olive+GR
thyme+Propolis+olive+GR As shown in FIG. 1, the prebiotic mixture of Propolis, thyme, olive and GR is capable of significantly reducing the formation of gas in the first 6 hours. Such effect, though less marked, but anyhow statistically significant, is also observed with the mixture of olive+GR.

As shown in FIG. 2, the amount of gas formed over 30 hours is essentially very similar in the various test tubes analyzed. This means that the extracts operate a delay in the fermentation kinetics, with a decrease of the formation of gas in the first hours of the process, and it is precisely this that contributes to decrease intestinal swelling and abdominal discomfort occurring in the first hours of ingestion of polysaccharide fibres.

In conclusion, therefore, said data clearly indicate how the mixtures described herein delay the inulin-induced gas formation kinetics, thereby increasing the tolerability of the fibres themselves in the intestine 4. Formulation of a Prebiotic Mixture In Table 1 below, an example of a prebiotic mixture in a tablet formulation according to the present invention is reported:

Inulin from chicory and/or from Jerusalem artichoke: 10-50%
*Althaea* root extract: 2-10%
Thyme leaf extract: 3-10%
Propolis extract: 3-10%
Olive leaf extract: 3-10%

5. Tablet Formulation Example fibres: abt. 1000-2000 g/day.
Propolis, lyophilized extract (EL): abt. 30-80 mg/day.
olive, lyophilized extract (EL): abt. 100-200 mg/day
thyme, lyophilized extract (EL): abt. 100-200 mg/day
Total of lyophilized extracts (thyme+olive+Propolis) per tablet: about 230-480 mg/day.

6. Example of Composition According to the Invention

Inulin: 35-70%
Jerusalem artichoke, pol.imp.bio: 15-40%
Thyme, lyophilized extract: 0.5-3.5%
*Aloe*, dry extract: 1-7%
Ginger, lyophilized extract: 1-6%
*Agrimonia* lyophilized extract: 3-12%
Olive, lyophilized extract: 5-15%

The invention claimed is:

1. A prebiotic mixture which delays and/or inhibits intestinal gas formation caused by one or more plant polysaccharide fibers therein comprising the following components:
   (i) at least one plant polysaccharide fibre;
   (ii) *Olea europaea* extract, Propolis extract, and *Aloe vera* extract; and
   (iii) *Thymus Vulgaris* extract and/or *Agrimonia eupatoria* extract,
   wherein said polysaccharide fibre is present in an amount of between 50% and 90% by weight of said mixture, and wherein components (ii) and (iii) are present in an overall amount of between 5% and 50% by weight of said mixture.

2. The prebiotic mixture according to claim 1, wherein said at least one plant polysaccharide fibre is selected from the group consisting of inulin, mucilages of Malvaceaes, flea-worth fibres, mucilages from *Linum usitatissimum*, glucomannan fibres, spear grass fibres, and gum arabic.

3. The prebiotic mixture according to claim 2, wherein said inulin is extracted from *Cichorium intybus* and/or *Helianthus tuberosus* and/or *Cynara scolymus* and/or *Taraxacum officinalis* and/or *Arctium lappa*.

4. The prebiotic mixture according to claim 2, wherein said mucilages of Malvaceaes are mucilages from *Malva silvestris* and/or mucilages from *Althaea officinalis*.

5. The prebiotic mixture according to claim 2, wherein said flea-worth fibres are fibres from seeds or cuticle of *Plantago psylium* and/or *Plantago indica* and/or *Plantago ovata*.

6. The prebiotic mixture according to claim 2, wherein said glucomannan fibres are fibres from *Amorphophallus konjac* tuber.

7. The prebiotic mixture according to claim 2, wherein said spear grass fibres are fibres from rhizome of *Cynodon dactylon* and/or *Elymus repens*.

8. The prebiotic mixture according to claim 2, wherein said at least one plant polysaccharide fiber comprises inulin, mucilages from *Althaea officinalis*, and gum Arabic; wherein component (iii) comprises the *Thymus vulgaris* extract.

9. The prebiotic mixture according to claim 2, wherein said at least one plant polysaccharide fiber comprises inulin, mucilages from *Althaea officinalis*, and gum Arabic; wherein component (iii) comprises the *Agrimonia eupatoria* extract.

10. The prebiotic mixture according to claim 1, wherein said fibres are at least 50, 60, 65, 70, 75, 80, 81, 82, 83, 84, 85, 86, 87, 88, 89, or 90% by weight of said mixture and said extracts are at least 5, 10, 12, 14, 16, 18, 20, 22, 24, 26, 28, 30, 35, 40, 45, or 50% by weight of said mixture.

11. A method for preventing and/or treating a gastrointestinal pathology that exhibits alteration of intestinal flora balance in a subject in need thereof comprising administering an effective amount of the prebiotic mixture according to claim 1 to said subject.

12. The method according to claim 11, wherein said pathology is selected from the group consisting of: diverticulosis, SIBO (small intestine bacterial overgrowth), IBD (inflammatory bowel disease), IBS (irritable bowel syndrome), traveller's diarrhoea, various dyspeptic forms, intestinal swelling, meteorism, diarrhoea caused by antibiotics, food allergies, and alteration of immune system defence.

13. A composition comprising a prebiotic mixture according to claim 1 and at least one excipient for preventing and/or treating a gastrointestinal pathology characterised by alteration of intestinal flora balance.

14. The composition according to claim 13, wherein said composition is in the form of a capsule, a tablet, a lozenge, a granulate, a powder, a syrup, an elixir, a hard gelatine, soft gelatine, a suspension, an emulsion, or a solution.

15. The composition according to claim 13, wherein said composition is in the form of a pharmaceutical composition, a nutraceutical composition, a dietary supplement, or a food.

16. The composition according to claim 13, wherein said pathology is selected from the group consisting of: diverticulosis, SIBO (small intestine bacterial overgrowth), IBD (inflammatory bowel disease), IBS (irritable bowel syndrome), traveller's diarrhoea, various dyspeptic forms, intestinal swelling, meteorism, diarrhoea caused by antibiotics, food allergies, and alteration of immune system defence.

* * * * *